United States Patent [19]
Dhadwal et al.

[11] Patent Number: 5,284,149
[45] Date of Patent: Feb. 8, 1994

[54] METHOD AND APPARATUS FOR DETERMINING THE PHYSICAL CHARACTERISTICS OF OCULAR TISSUE

[76] Inventors: Harbans S. Dhadwal, 6 Ben Pl., Setauket, N.Y. 11733; Rafat R. Ansari, 18313 Chagrin Blvd., Shaker Hts., Ohio 44122

[21] Appl. No.: 824,590

[22] Filed: Jan. 23, 1992

[51] Int. Cl.$^5$ .............................................. A61B 3/10
[52] U.S. Cl. ................................. 128/665; 128/745
[58] Field of Search .......................... 128/633–634, 128/645, 652, 664–665, 745; 351/221

[56] References Cited

U.S. PATENT DOCUMENTS

| | | | |
|---|---|---|---|
| 4,350,163 | 9/1982 | Ford, Jr. et al. | 128/633 |
| 4,485,820 | 12/1984 | Flower | 128/633 |
| 4,573,778 | 3/1986 | Shapiro | 128/633 |
| 4,702,576 | 10/1987 | Magnante | 351/221 |
| 4,776,687 | 10/1988 | Nakanishi et al. | |
| 4,836,207 | 6/1989 | Bursell et al. | |
| 4,957,113 | 9/1990 | Benedek | |
| 4,993,827 | 2/1991 | Benedek et al. | |
| 5,025,785 | 6/1991 | Weiss | 128/633 |
| 5,072,731 | 12/1991 | Taratata et al. | 128/633 |

*Primary Examiner*—Kyle L. Howell
*Assistant Examiner*—Angela D. Sykes
*Attorney, Agent, or Firm*—Hoffmann & Baron

[57] ABSTRACT

A method and apparatus for determining the physical characteristics of ocular tissue is provided. A lens-less monomode fiber is caused to generate an expanding beam of monochromatic laser light into ocular tissue such that the light is scattered by the tissue in the backward direction. A second optical fiber, which is multimode at the wavelength of the light passing through the monomode transmission fiber, coherently detects light scattered by the ocular tissue. The scattered light received by the second optical fiber is converted into an electrical signal, which is subsequently analyzed to determine whether changes in the molecular structure of the ocular tissue have occurred.

15 Claims, 13 Drawing Sheets

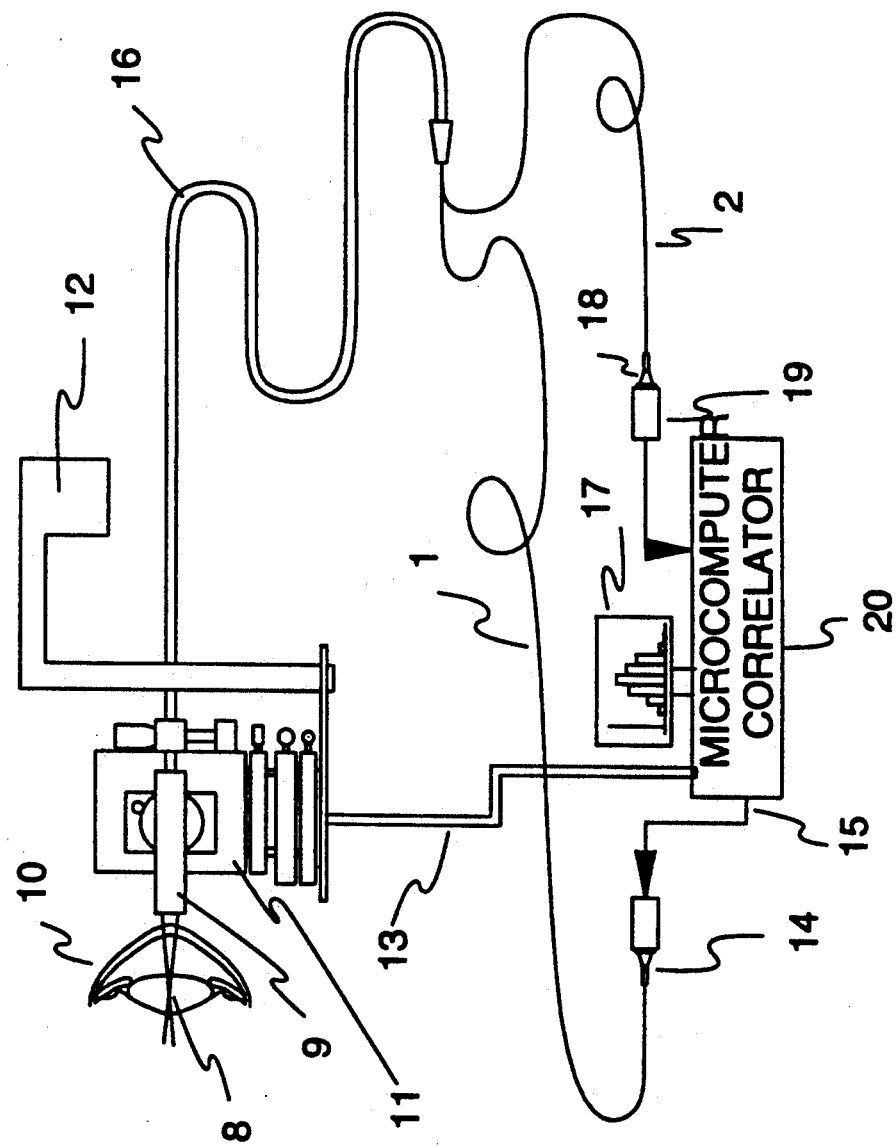

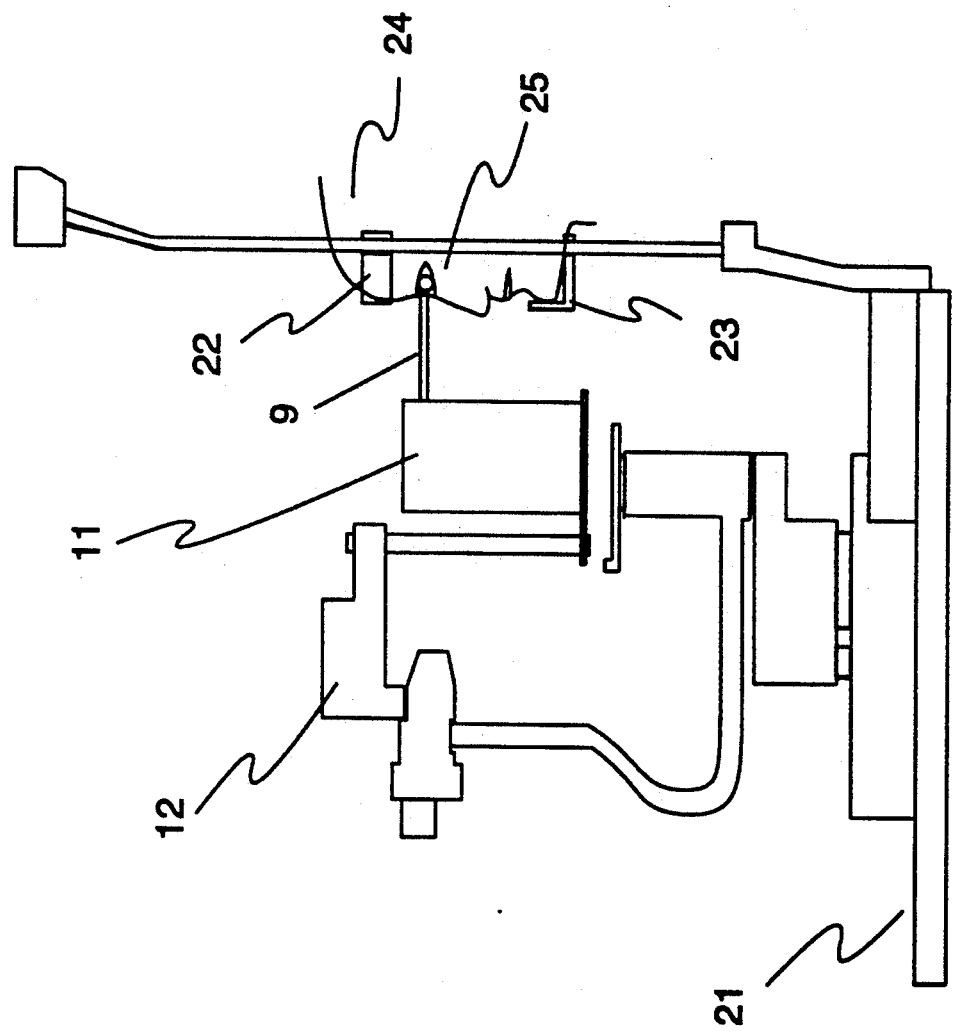

METHOD AND APPARATUS FOR DETERMINING THE PHYSICAL CHARACTERISTICS OF OCULAR TISSUE

BACKGROUND OF THE INVENTION

1. Field of the Invention

A fiber optic based dynamic light scattering apparatus is disclosed for in-vivo characterization of the concentration and size of various protein macromolecules in the anterior segment of the eye, which includes the crystalline lens, the aqueous humor and the cornea. A lens-less fiber optic probe comprising two optical fibers may be fixed onto an aplanation tanometer mount, which is a universal accessory to any commercial slit lamp microscope. A monomode optical fiber guides light from a semiconductor laser source to a point inside the eye lens, and a second optical fiber, positioned in close proximity, is used for coherent detection of the scattered light in the backward direction. The free end of the receiving optical fiber is connected to a photodetector, typically a photomultiplier. In this manner, light is detected and converted into a pulse position modulated electrical waveform, which is processed by a digital correlator to yield the first order electric field autocorrelation of the scattered laser light. Subsequent inversion of the data yields a distribution of diffusion coefficients, which can be scaled to give a distribution of particle size or molecular weight. The ability to track small changes in concentration and size are vital for the early detection and prevention of ocular disorders, such as cataractogenesis.

2. Brief Description of the Prior Art

Cataract surgery is inevitable in many humans because of the changes caused to the transparency of the eye due to aging. Other known factors such as high blood sugar levels and long exposure to ultra violet light can accelerate this process. Current state-of-art systems, which include visual inspection through a slit lamp microscope or analysis of a photographic plate, lack the sensitivity to detect small molecular changes in the ocular tissue. Early detection of changes in relative concentration and size of the different protein species will permit development of preventive therapy, and possible reversal of cataractogenesis. A reliable apparatus for non-invasive, rapid, quantitative and causing the least trauma to the patient, has been long sought goal for the study of cataractogenesis and other ocular disorders.

In the last three decades, following the invention of the laser, light scattering (LLS) has become an indispensable, non-invasive, and extremely sensitive technique for routine characterization of molecular changes in physiological, chemical, polymer and colloidal systems. A conventional light scattering apparatus requires illumination of the sample by a coherent source, detection of the weak scattered light at some specified scattering angle, processing of the data and inversion to yield the required information of size and shape. Until recently, conventional LLS systems, because of their large size and sensitivity to vibrations, were confined to a research laboratory. However, in the last five years, significant advances have been made in the miniaturization of these systems by utilizing fiber optics, semiconductor laser sources and detectors. Data acquisition and analysis have also been dramatically improved due to rapid technological advances in the microelectronics industry.

LLS, in particular dynamic light scattering (DLS) or quasielastic light scattering, or intensity fluctuation spectroscopy, or photon correlation spectroscopy, has been successfully used for the characterization of protein macromolecules in excised eye lenses, however, a clinical apparatus in still not available. Benedek [U.S. Pat. No. 4,957,113] and Benedek and Magnante [U.S. Pat. No. 4,993,827] have disclosed an apparatus and a method for detection of ophthalmic diseases, respectively. Their apparatus comprises a conventional light scattering system, with all its inherent alignment and stability problems. A person skilled in the art usually requires several hours to align a conventional DLS apparatus. Analysis techniques described in the latter patent have been employed by researchers for the last two decades and have been commercially available for many years.

Other apparatus pertaining to the detection of ophthalmic diseases are not based on dynamic light scattering, and therefore do not provide information on the molecular changes of the protein macromolecules. U.S Pat. Nos. 4,776,687 and 4,854,693 disclose such apparatus.

SUMMARY OF THE INVENTION

The present invention provides a method and an apparatus for in-vivo diagnostics of the eye using a compact light scattering system requiring no alignment, no moving parts, and no lenses. The optical system is very rugged, flexible, and compact. Micrometer stages, which can be mounted onto a universal aplanation mount, provide precise location of the scattering volume for repeatable measurements from any region in the anterior segment of the eye.

The present invention further provides an in-vivo assembly for measuring the distribution in diffusion coefficients and relative concentrations of various protein macromolecules in the anterior segment of the eye. The assembly comprises:

a fiber optic probe for delivering monochromatic laser light, the probe including a probe body, a lens-less, transmitting fiber for transmitting an expanding beam of laser light, and a lens-less, receiving optical fiber for coherently detecting scattered light, the transmitting and receiving fibers being mounted to the probe body such that an end of said receiving fiber is positioned in close proximity to an end of the transmitting fiber for coherently detecting the scattered laser light at an angle in the range 90° to 175°;

a photon detector connected to the receiving fiber for converting a train of photon pulses into photoelectron pulses;

a digital correlator for obtaining the first order electric field autocorrelation of the scattered light detected by the receiving fiber, and means for analyzing the first order electric field autocorrelation to determine the distribution in diffusion coefficients, and hence size.

A plurality of probes are preferably provided with the assembly, each with the optical fiber ends oriented at different angles. Different probes are employed depending upon the depth at which the ocular tissue is to be examined.

A method according to the invention includes the steps of causing a lens-less fiber to deliver an expanding beam of monochromatic laser light to ocular tissue, detecting back scattered laser light through a lens-less, multimode optical fiber positioned in close proximity to the lens-less, light-transmitting fiber, converting the detected light to electrical signals, and analyzing the electrical signals to determine whether changes in the molecular structure of the ocular tissue have occurred.

BRIEF DESCRIPTION OF THE DRAWINGS

FIG. 6 is a schematical illustration which shows a clinical apparatus for characterization of the size of protein constituents in the transparent regions of anterior portion of the eye according to the invention;

FIG. 6A is a schematic illustration showing the modification of a slit lamp microscope according to the invention.

DETAILED DESCRIPTION OF THE INVENTION

Figure 1:
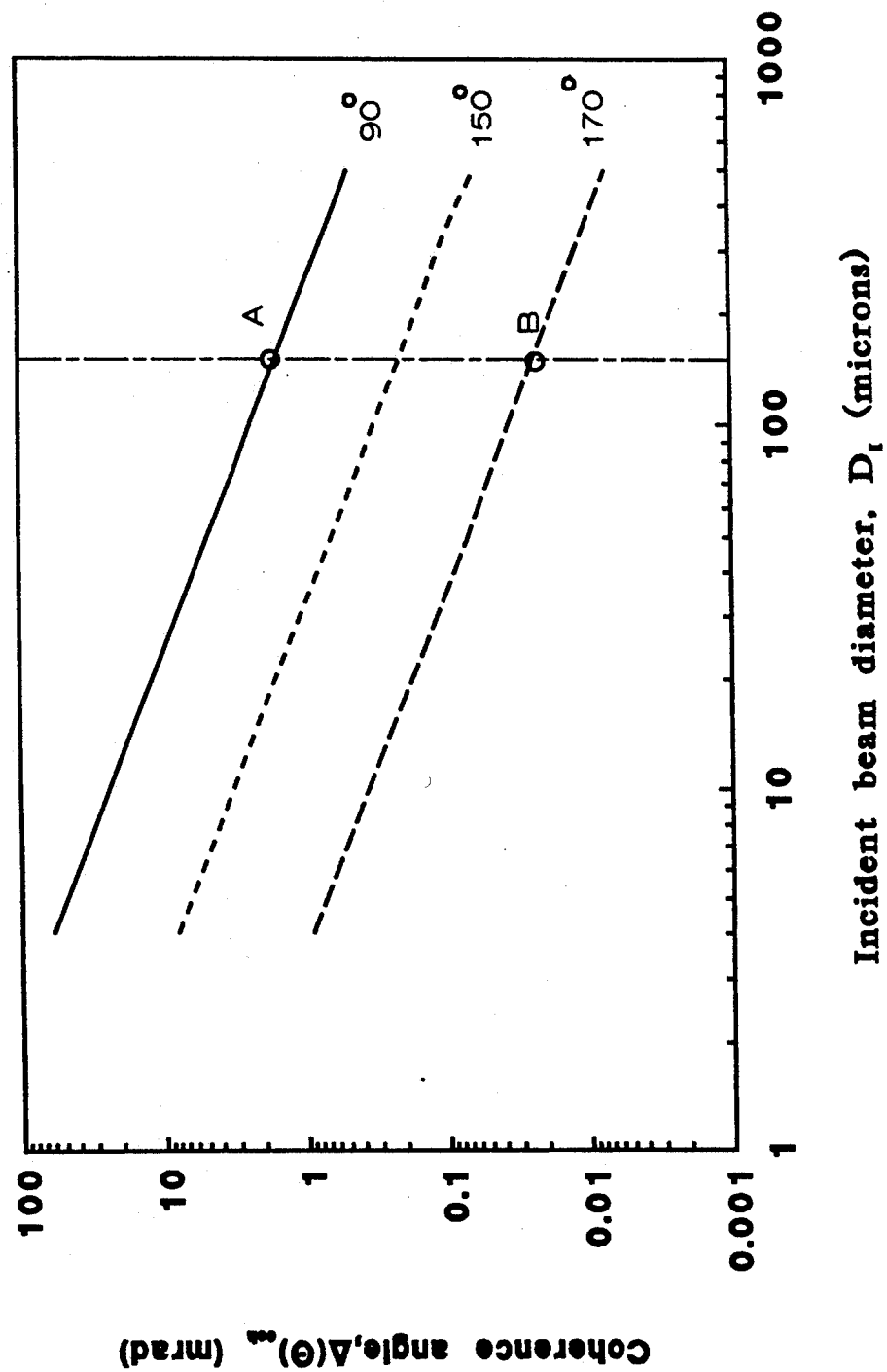
FIG. 1 is a graph illustrating the spatial coherence requirements for efficient self-beating detection of scattered laser light.

Brownian motion is a term used to describe many physical phenomena in which some quantity is continuously undergoing random fluctuations. It is used to described the countless diffusion processes occurring in many diverse disciplines from the motion of electrons and holes in semiconductor devices, to the motion of macromolecules and colloids in chemical systems, to the motion of macromolecules, such as proteins, in physiological systems, to the motion of pollutants in the atmosphere. The motion was first observed in 1828 by Robert Brown, and theoretically predicted by Albert Einstein in 1905, however, it was not until the discovery of the laser that Brownian motion became synonymous with quasielastic light scattering, or dynamic light scattering or intensity fluctuation spectroscopy or photon correlation spectroscopy. All of these refer to the same laser based probing technique which provides a measurement of the size (hydrodynamic radius or molecular weight) of particles undergoing Brownian motion.

The variance of particle displacement for a collection of particles undergoing Brownian motion derived from Langevin's equation is $$\sigma_x^2(t) = \frac{2kT}{\xi}\left\{1 - \frac{m}{\xi}\left[t - \exp\left(-\frac{\xi}{m}t\right)\right]\right\}, t \geq 0 \quad (1)$$

where m is the particle mass, $\xi$ is the coefficient of friction, T is the absolute temperature, and k is Boltzman's constant.

$$\text{For } t < < \frac{m}{\xi} \quad (2)$$

$$\sigma_x^2(t) = \frac{kT}{m} t^2.$$

Particles move with constant velocity and thus behave as free particles. For time $$t < < \frac{m}{\xi} \quad (3)$$

$$\sigma_x^2(t) = \frac{2kT}{\xi} t.$$

Particles experience viscous drag through collisions with the macromolecules of the surrounding medium. The first order electric field autocorrelation of laser light scattered from particles executing Brownian motion is $$g^{(1)}(t) = \exp\left[-\frac{Q^2\sigma_x^2(t)}{2}\right] \quad (4)$$

where $$Q = \frac{4\pi\eta_3}{\lambda_o}\sin\left(\frac{\theta}{2}\right)$$

is the scattering wavenumber, $\theta$ is the scattering angle, $\lambda_o$ is the free space wavelength of light and $\eta_3$ is the refractive index of the medium in which the particles are suspended.

The normalized first order electric temporal autocorrelation of the fluctuation in the scattered light amplitude due to particles undergoing Brownian motion, in the viscous regime, is $$g^{(1)}(t) = \exp(-Q^2Dt)$$

For spherical particles, the Stokes-Einstein relation expresses D, the translational diffusion coefficient, as a function of hydrodynamic radius r of the particle, $$D = \frac{kT}{\xi} = \frac{kT}{6\pi\eta r}$$

where $\eta$ is the viscosity of the medium. A self-beating experiment involves a measurement of an intensity-intensity temporal autocorrelation, $G^{(2)}(t)$, which for Gaussian statistics is related to $g^{(1)}(t)$ through the Siegert relation $$G^{(2)}(t) = A[1 + B|g^{(1)}(t)|^2]$$ (b 5)

where $\beta$ describes the spatial coherence of the scattering volume, and A is the baseline.

For a monodisperse sample the measured intensity-intensity autocorrelation decays exponentially with a time constant 2QD, and a simple transformation yields the particle size. However, for a polydisperse system the first order autocorrelation is $$g^{(1)}(t) = \int_a^b p(D)e^{-Q^2 Dt} dD \quad (6)$$

where p(D) is the distribution in diffusion coefficient due to species present in the solution, and a and b are the lower and upper bounds on D, respectively. The above equation represents an ill-posed inversion problem in the presence of additive noise which is unavoidable in experimental accumulation of data. The Stokes-Einstein relation together with a knowledge of the scattering strengths from each size species leads to a particle size distribution from p(D). Commercial software, using various established techniques, is available for inverting Eqn(6) to yield a distribution in size.

Dynamic light scattering is concerned with measuring the intensity-intensity temporal correlation of the light scattered from particles illuminated by a monochromatic light source. In order to observe the modulation imparted by tee particles undergoing Brownian motion, the scattered light must be collected over a well defined coherence solid angle, which is a function of the size of the scattering volume.

The spatial coherence requirements for efficient self-beating translate into an uncertainty in the scattering angle as defined by the detection geometry. For cylindrical incident and detection beams of diameter $D_I$ and $D_A$, respectively, the planar coherence solid angle, assuming $D_A > D_I$, is given by $$(\Delta\theta)_{coh} = \frac{\lambda \sin^2(\theta)}{2D_I\left[\frac{D_A}{D_I} + |\cos(\theta)|\right]} \quad (7)$$

FIG. 1 shows a plot of $(\Delta\theta)_{coh}$ as a function of $D_I$ for various values of the scattering angle, assuming a wavelength of 0.475 μm in water and $$\frac{D_A}{D_I} = 1. \text{ Values of } \frac{D_A}{D_I}$$

greater than unity result in more stringent requirements for $(\Delta\theta)_{coh}$. In a typical DLS experiment, a detection geometry using spherical lenses and apertures, an angle $(\Delta\theta)_{coh}$ of 1.6 mrad(0.1°) may be obtained with some difficulty. The corresponding value $D_I$, at a scattering angle of 90°, is 150 μm (point A in FIG. 1). However, at 170°, for the same incident beam diameter, $(\Delta\theta)_{coh} = 0.39$ mrad (0.02°), point B in FIG. 1, is beyond practical considerations for conventional laser light scattering systems (LLS). Based on these observations, compact cylindrical fiber probes comprising an optical fiber and a graded index microlens have been constructed, as described in U.S. Pat. No. 4,983,040. Optimization of the fiber optic probes, for both DLS and static light scattering, can be achieved at each scattering angle. However, these probes alone are not suitable for a self contained back scatter system which is necessary for a real time clinical apparatus for the study of ocular disorders.

From the above analysis it can be ascertained that spatial coherence requirements are most stringent in the back scatter regime. In fact, in the limit $\theta \to \pi$, $(\Delta\theta)_{coh} \to 0$, however, in practice the effective penetration depth into the sample places a lower bound on the value of $(\Delta\theta)_{coh}$. Typically, for a weakly absorbing medium, the effective penetration depth is fifteen times the core diameter. Even under these conditions a monomode optical fiber, without additional optics, is not suitable as a coherent back scatter receiver.

An optical fiber with a numerical aperture of 0.1 in air gives an uncertainty angle of about 75 mrad(4.3°) in water. In order to use this optical fiber as a coherent receiver having a high self-beating efficiency, without additional optics, the incident beam diameter in the center of the scattering volume, computed using Eqn. (7), must be less than 0.05 μm and 3 μm for $\theta = 170°$ and for $\theta = 90°$, respectively. A conventional LLS system can be designed to achieve the latter condition with considerable difficulty. However, a monomode optical fiber with a core diameter equal to about four microns may be useful for delivering a narrow, but rapidly diverging optical field to the scattering volume.

An unnecessarily large numerical aperture leads to reduced resolution in particle size. In the limit of a point scattering volume, requirements on the coherence solid angle imply that an infinite aperture detection system could be employed. Setting aside the extremely weak signal strength from a point scatterer, the resultant uncertainty in scattering angle will lead to an unacceptable error in particle size. An uncertainty $\Delta r$ in particle size can be expressed as a function of the scattering angle and the uncertainty $\Delta\theta$ in the scattering angle, $$\frac{\Delta r}{r} = 1 - \left[\cos\left(\frac{\Delta\theta}{2}\right) - \sin\left(\frac{\Delta\theta}{2}\right)\cot an\left(\frac{\theta}{2}\right)\right]^2 \quad (8)$$

In the limit $$\theta \to \frac{\pi}{2}, \left[\frac{\Delta r}{r}\right] \to \sin(\Delta\theta),$$

and as $$\theta \to \pi, \left[\frac{\Delta r}{r}\right] \to \sin^2\left(\frac{\Delta\theta}{2}\right).$$

Thus at $\theta = 90°$ an optical fiber with a numerical aperture of 0.1 in air leads to a 7.5% error in particle size (in water). However, $\theta = \pi$ the same uncertainty produces an error of only 0.14% in particle radius. State of the art DLS systems can reproducibly measure particle size to within 1%. Clearly, use of a monomode optical fiber, without additional control of the numerical aperture, will lead to an unacceptably large error in particle size, except near back scatter.

Theoretical modeling of DLS is based on the assumption of quasimonochromatic and plane wave incidence. Departure from this condition may lead to ambiguities in data interpretation. Conventional light scattering systems meet this requirement by confining the scattering to the focussed region of an incident laser beam. An unfocussed laser beam, though highly collimated, is not used because of the larger diameter (typically > 1 mm). The ideal incident beam should have a diameter less than 100 μm and divergence less than 1 mrad. Delivery of a laser beam by means of a lens-less optical fiber requires careful consideration, and in particular, the use of an unlensed optical fiber, which has a divergence angle of 80 mrad, goes against the accepted body of knowledge in DLS.

The near field distribution of the optical field emanating from the tip of a monomode optical fiber, excited by a spatially coherent quasimonochromatic source, is adequately described by a Gaussian distribution, thereby permitting the use of Gaussian optics to characterize and predict the expansion of the optical field away from the tip. The beam radius, w(z), and the radius of curvature, R(z), at a distance z from the beam waist is given by $$w(z) = w_o \left[ 1 + \left( \phi \frac{z}{w_o} \right)^2 \right]^{\frac{1}{2}} \quad (9a)$$

$$R(z) = z \left[ 1 + \left( \frac{1}{\phi} \frac{w_o}{z} \right)^2 \right] \quad (9b)$$

where $w_o$ is the beam waist, (=core radius of the monomode optical fiber);

$$\phi = \frac{\lambda}{\pi w_o}$$

is the divergence angle. The above equation indicates that a narrow optical beam can be delivered into the scattering volume by means of a monomode fiber having a core radius equal to about two μm, however, at the expense of a rapidly changing radius of curvature of the incident laser beam, analogous to the situation of a highly focussed laser beam. It has been shown that the effects due to phase and amplitude variations of a collimated or focussed laser beam are minimal in the back scatter regime. Distortions in the autocorrelation are pronounced, particularly in the forward scattering direction, when focusing by a 50× (or higher power) microscope objective. This means that for a monomode optical fiber having a numerical aperture of 0.1, corresponding to a 5× microscope objective, the affects of phase and amplitude variations are not a serious concern.

A lens-less probe comprised of two or more optical fibers exploits the relaxed spatial coherence requirements when the incident laser beam has a small cross-section, typically less than twenty microns. The benefits of the subsequent geometry are considerable, ranging from a reduction in size by one order of magnitude, to design flexibility which allows the center and size of the scattering volume as well as the scattering angle to be controlled by the designer.

Figure 2:
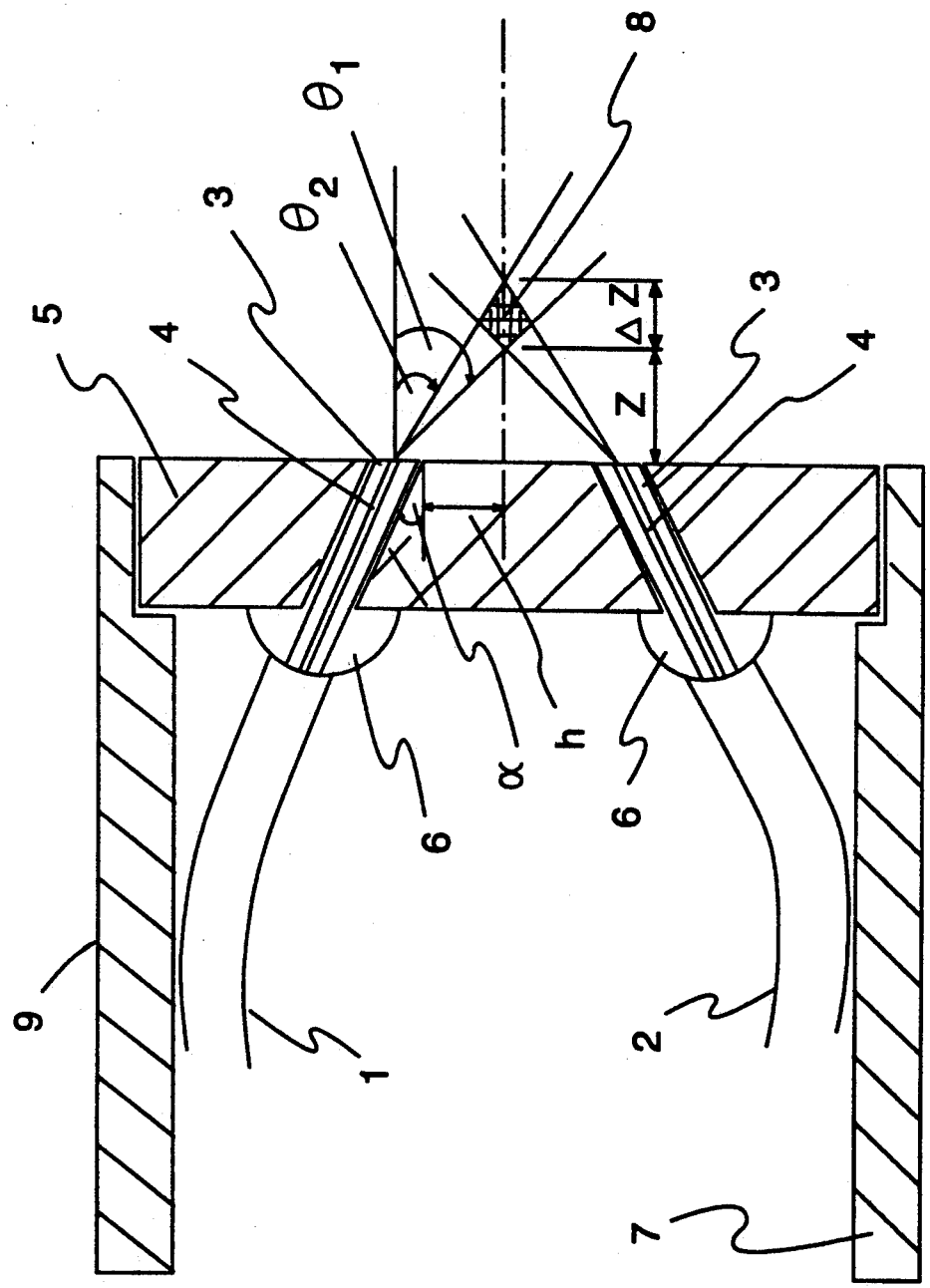
FIG. 2 is an enlarged, schematical illustration of a fiber optic transmitting/receiving probe employed in accordance with the invention.

FIG. 2 provides a detailed schematic illustration of a fiber probe 9 utilizing a monomode optical fiber 1 and a multimode optical fiber 2, which are mounted into a specially designed stainless steel ferrule comprised of two parts, a face plate 5 and a cylindrical housing 7. The optical fibers 1,2 are attached to the face plate using epoxy 6. In constructing a particular probe, one can define the edge of the scattering volume 8 at Z; the length of the scattering volume, ΔZ; the scattering angle θ (in the range 90° to 175°). The relevant equations $$\theta = \pi - 2\text{Sin}^{-1}\left[ \frac{n_1}{n_2} \text{Sin}(\alpha) \right] \quad (10)$$

$$Z = \left[ h + \frac{D_f}{2\text{Cos}(\alpha)} \right] \frac{1}{\text{Tan}(\theta_1)} \quad (12)$$

$$\Delta Z = \left[ h + \frac{D_f}{2\text{Cos}(\alpha)} \right] \left[ \frac{1}{\text{Tan}(\theta_2)} - \frac{1}{\text{Tan}(\theta_1)} \right] \quad (13)$$

$$\text{Sin}(\theta_1) = \frac{n_1}{n_2} \text{Sin}(\alpha + \rho) \quad (14)$$

$$\text{Sin}(\theta_2) = \frac{n_1}{n_2} \text{Sin}(\alpha - \rho) \quad (15)$$

$$\rho = \text{Cos}^{-1}\left( \frac{n_3}{n_1} \right) \quad (16)$$

$$\frac{n_3}{n_1} = \left[ 1 - \left( \frac{NA}{n_1} \right)^2 \right]^{\frac{1}{2}} \quad (17)$$

Figure 3:
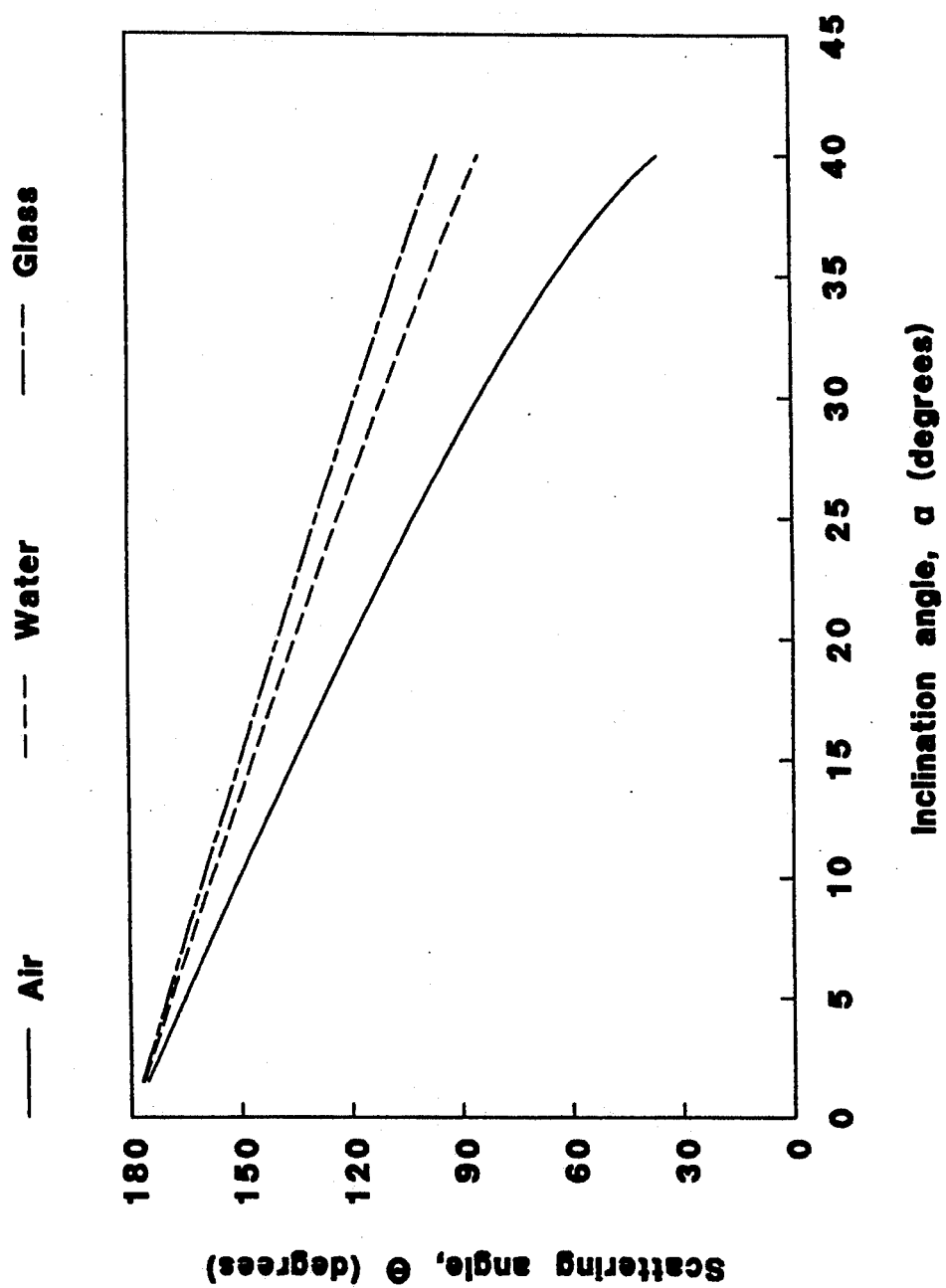
FIG. 3 is a graph illustrating the scattering angle inside the eye lens, as a function of the inclination angle of the optical fiber above the optical axis.
Figure 4:
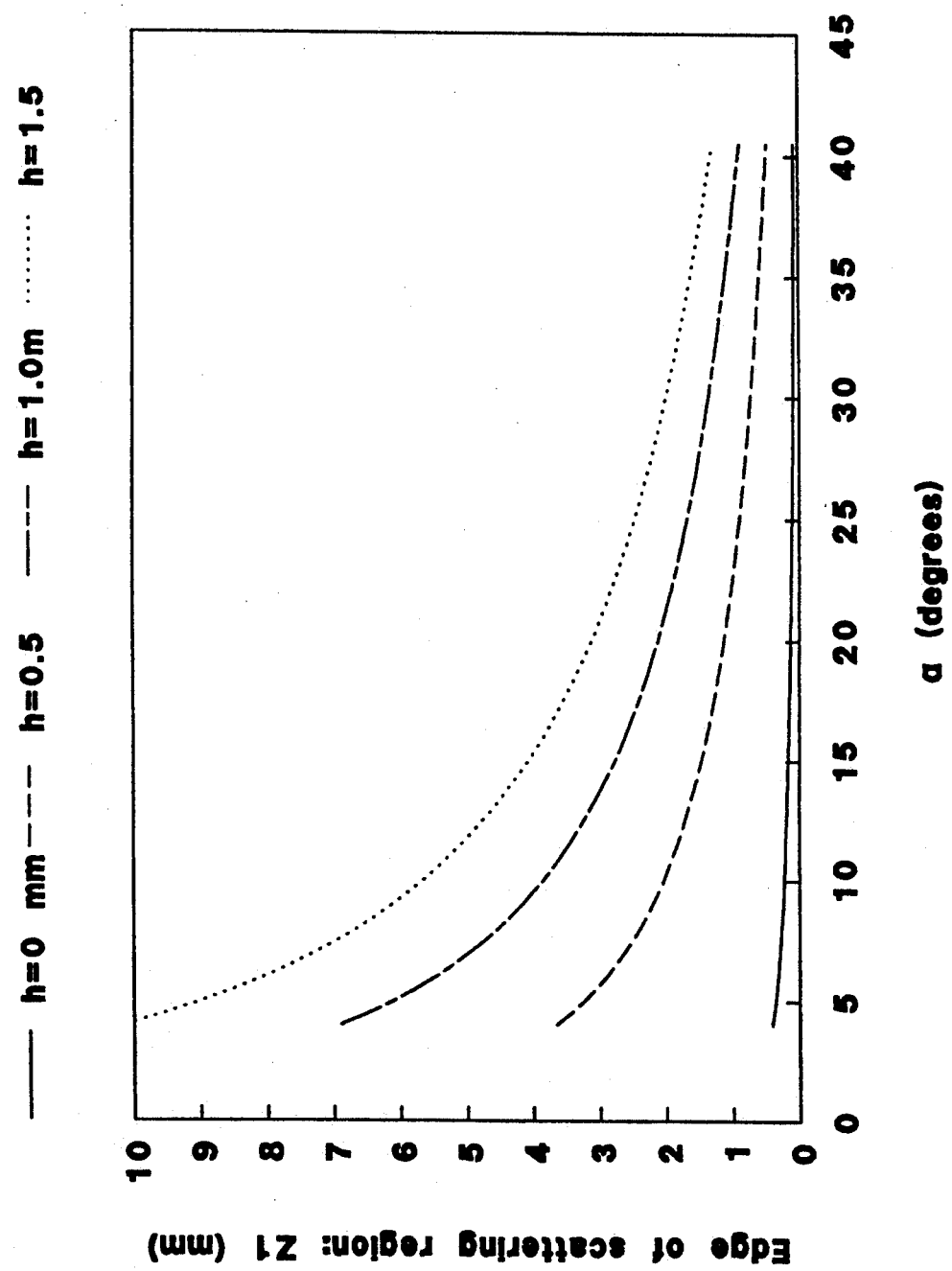
FIG. 4 illustrates the position of the edge of scattering region inside the eye lens as a function of the inclination angle of the optical fiber above the optical axis.
Figure 5:
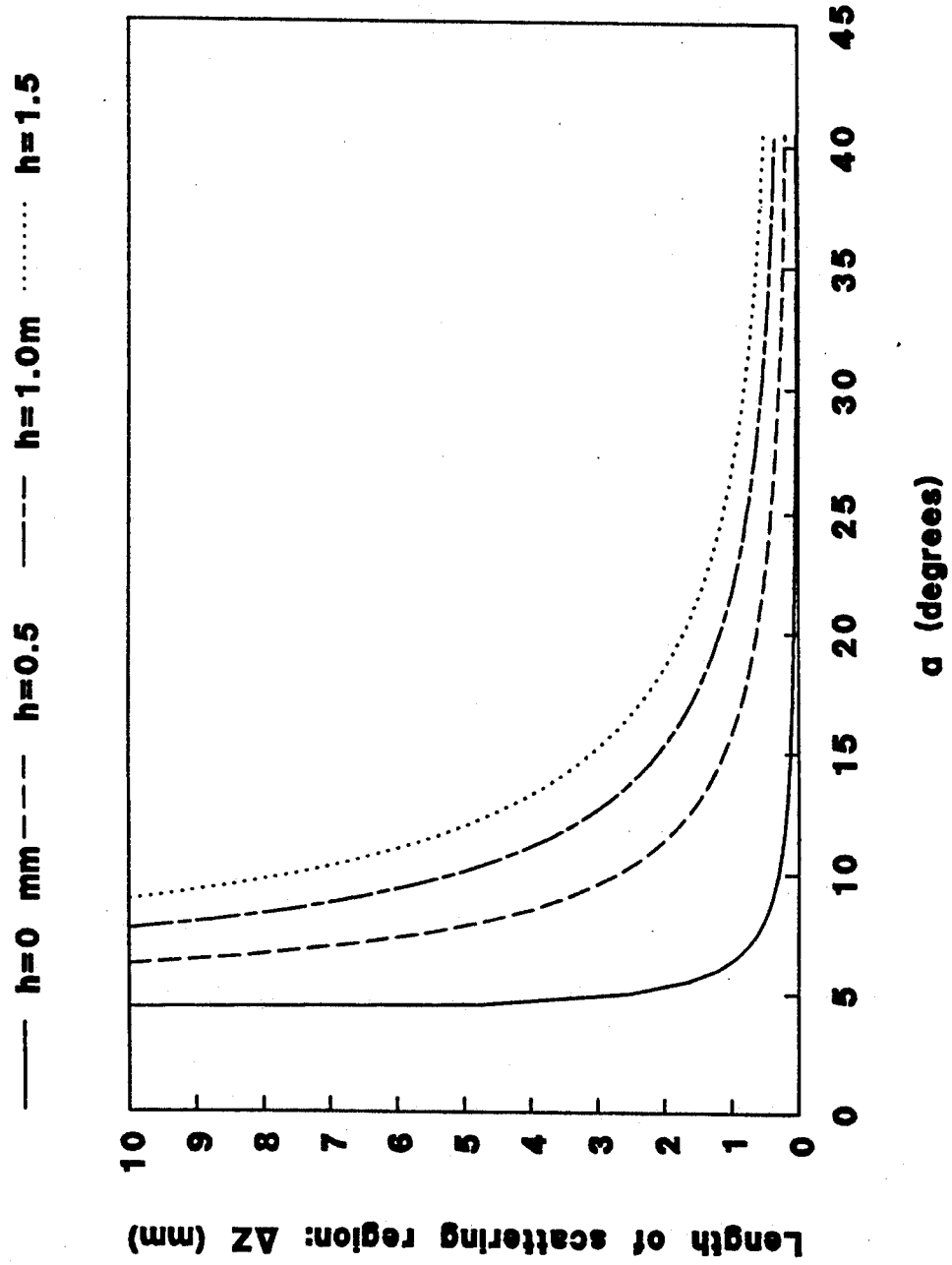
FIG. 5 illustrates the length of the scattering region inside the eye lens as a function of the inclination angle.

In the above equations, $n_1$, $n_3$, and $n_2$ are refractive indices of the optical fiber core 4, cladding 3, and the suspension medium, respectively. $D_f$ and NA are the cladding diameter and numerical apertures, respectively of the two optical fibers assumed to be identical. In practice, the transmitting optical fiber is monomode at the operating wavelength, but the receiving optical fiber is slightly multimode. All other variables are as indicated in FIG. 2. Based on the above set of equations a lens-less probe can be designed to meet constraints imposed by the position and volume of the scattering region, as well as any scattering angle in the range 90° to 175°. FIGS. 3, 4, and 5 show the possible range of scattering angle, edge of the scattering region from the probe tip, and the length of the scattering region, respectively, as a function of the inclination angle, α and the height h, of the optical fiber above the optical axis.

In accordance with this invention, a novel clinical apparatus as shown in FIG. 6, for in-vivo characterization of ocular tissues, is provided. Existing state-of-art systems employ distributed bulk optics and are subsequently rather complex in structure. The fiber probe 9, together with a micro-positioner 11, e.g. a micrometer stage, can be fixed onto a universal applanation tonometer mounting assembly 12. This arrangement provides precise location of the scattering volume 8 in any substantially transparent region of the anterior segment of the eye 10. Position information is issued from a microcomputer 20, via control lines 13. The transmitting monomode optical fiber 1 is pig-tailed to a semiconductor laser 14, and threaded through a ruggedized cable assembly 16, which also contains the receiving optical fiber 2. The semiconductor laser 14 is preferably coupled to the microcomputer by a connector 15. The free end of the receiving fiber is terminated with another connector 18, which allows easy coupling to a photodetector 19. The connector 18 allow the probe 9 and laser 14 to be easily disconnected from the apparatus and replaced by another probe and associated laser. As the angle between the fibers within the probe determines the location of the scattering volume, different probes can be used to study different portions of the anterior segment of the eye. For example, one probe can be designed primarily for use in studying the cornea where a high scattering angle (e.g. about 175°) would be employed. Another probe or set of probes may be employed for studying the lens, which requires a much lower scattering angle. A monitor 17, is used for displaying all the relevant information pertaining to the experiment.

FIG. 6A shows the incorporation of the fiber optic probe 9 into a slit lamp microscope assembly 21. A patient's head 24 is positioned into the slit lamp 21 by means of forehead and chin restraints 22 and 23, respectively. The computer controlled micrometer stages 11, mounted on the aplanation tanometer mount 12, allows precise positioning of the fiber probe 9 in front of the patient's eye 25.

Figure 7:
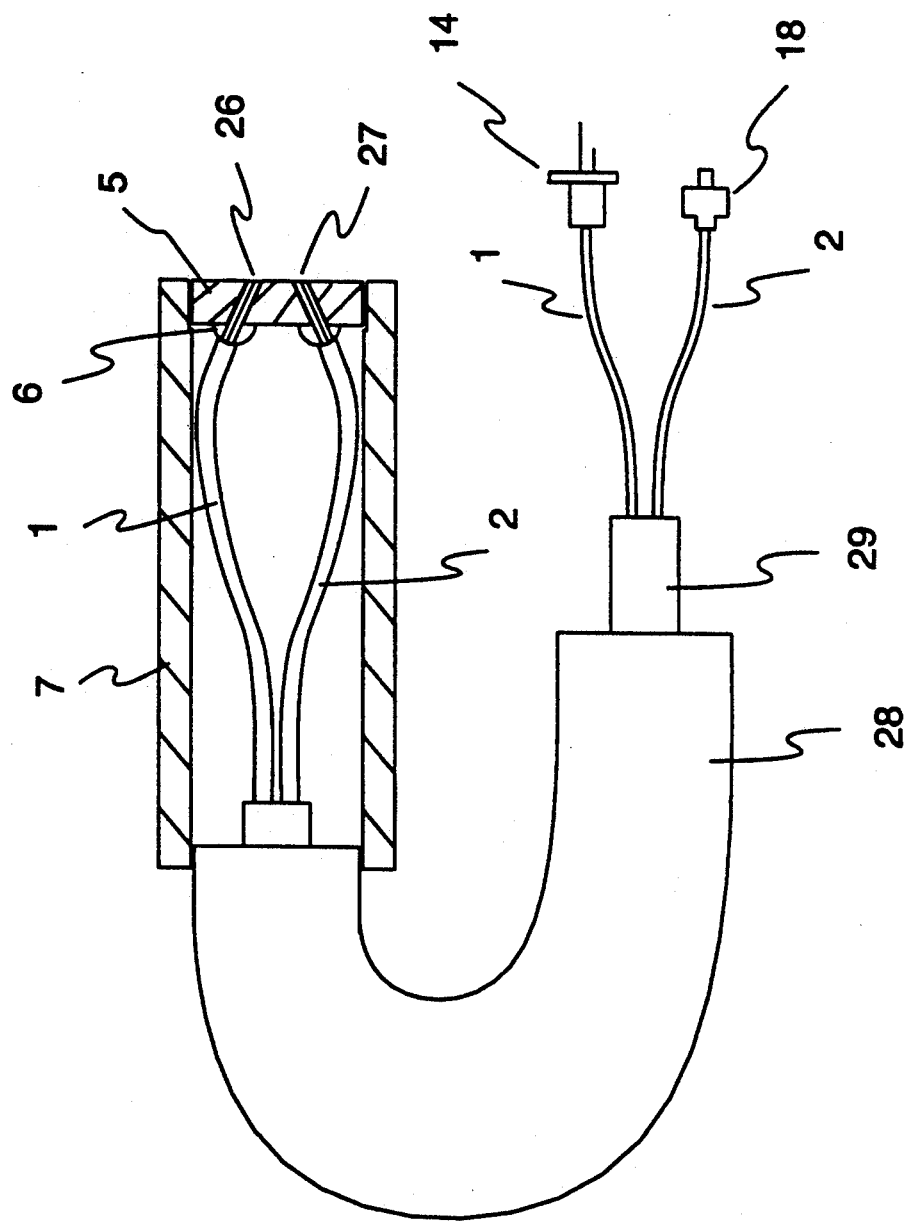
FIG. 7 is a schematic illustration of a dynamic light scattering apparatus employed in the clinical apparatus shown in FIG. 6 and FIG. 6A.

The DLS portion of the apparatus is shown in FIG. 7. It is no more than 5 mm in diameter, and can be held in the palm of one hand (FIG. 7 accordingly provides a greatly enlarged view thereof). The monomode optical fiber 1 is pig-tailed to a semiconductor laser 14 operating at a wavelength of, for example, 670 nm. The monomode optical fiber is threaded through a protective Teflon tubing 29, and an outer pvc coated monocoil tubing 28, for ruggedization. A bare portion of the monomode optical fiber is epoxied into a precision machined hole 26. The monomode optical fiber delivers an expanding Gaussian laser beam to the scattering region. Laser light scattered in the backward direction, (scattering angle in the range of 90° to 175°), is detected by the second optical fiber 2, which is positioned in a second hole 27, in close proximity to the transmitting optical fiber 1. The receiving multimode optical fiber decreases the overall time required to accumulate the intensity-intensity temporal correlation but with a sufficiently good signal-to-noise ratio, permitting the recovery of the size distribution. The reduction in time adds to patient comfort.

The end faces of both fibers 1, 2 are substantially coplanar with the outer surface of the face plate 5. The receiving fiber 2 is threaded through the same Teflon sleeving 29, and monocoil tubing 28, up until the point where the transmitting and receiving fibers are separated. The latter is terminated in a connector 18, which can be mated directly to a photoconductor (e.g. photodetector 19) for converting a train of photon pulses into a pulse position modulated electrical waveform. The invention accordingly provides a unique implementation of a DLS optical system which requires no lenses, no moving parts, no alignment, and is insensitive to any vibrations or other forms of interference. The transmitting and receiving fibers 1, 2 require no lenses, are permanently locked in position in the probe, and can simply be moved into position adjacent to the eye by operating the micropositioner 11.

By providing a beam which begins expanding from the end of an extremely small optical fiber, the light which reaches the retina is even more diffused than that of a beam which is focussed within the ocular tissue. The apparatus 10 is accordingly very safe to use. The divergence angle of the laser beam leaving the posterior surface of the eye lens is at least a factor of fifteen larger than that used in existing systems.

An experimental prototype of the invention has been used to investigate the formation a reversible "cold" cataract induced in excised bovine eye lenses and age dependent cataractogenesis in excised human eye lenses. The results have been summarized below and confirm that changes in the size of protein macromolecules is an early indication of opacity in the crystalline lens. The technique is very sensitive and will detect any changes in size induced by the normal aging process, or by drug therapy, and therefore can play a vital role in the prevention and detection of cataractogenesis.

Figure 8:
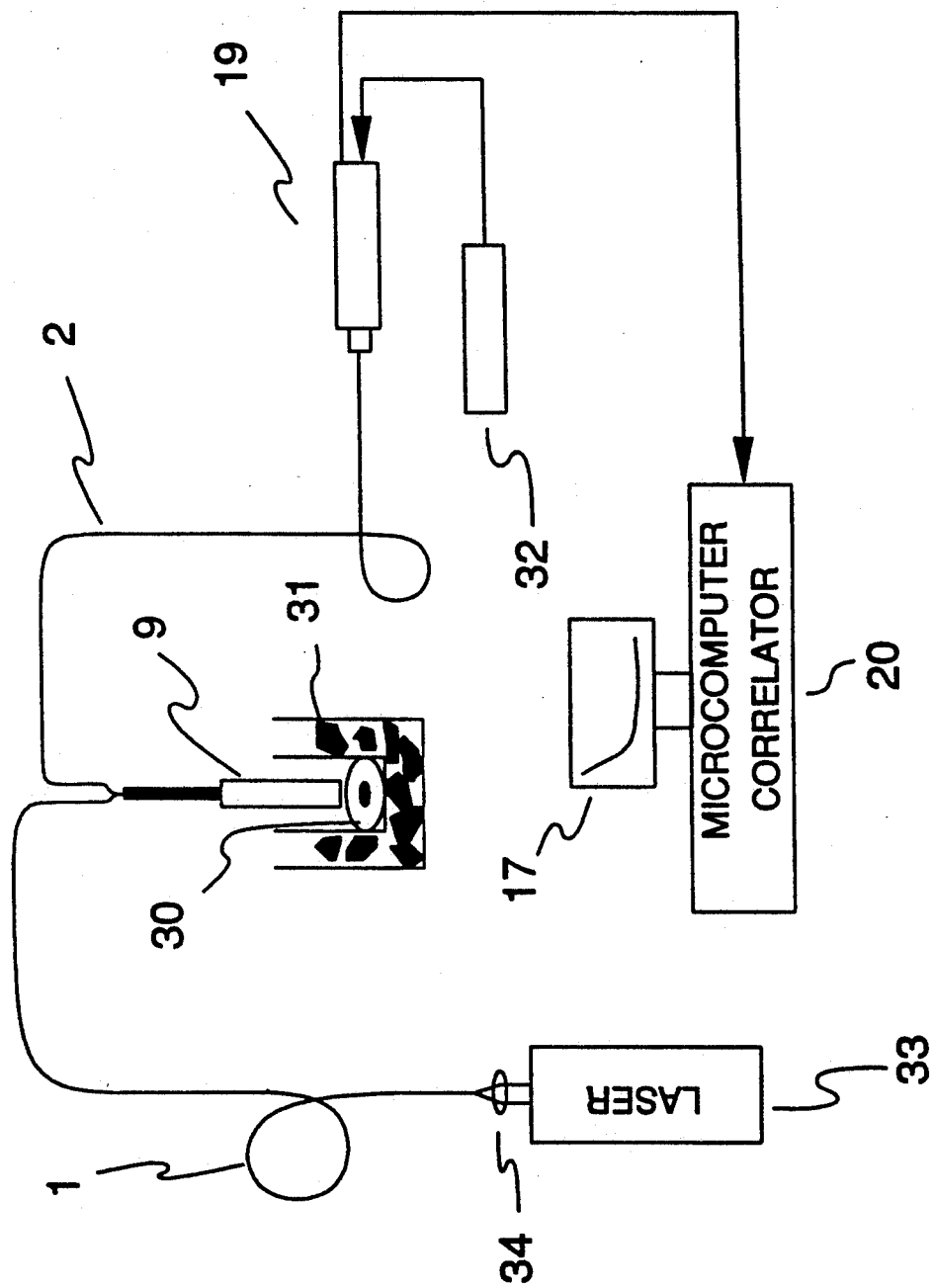
FIG. 8 is a schematic illustration of an apparatus according to the invention used for characterization of protein size in excised bovine and human eye lenses.

FIG. 8 shows a prototype implementation of the invention disclosed herein. Light from a helium neon laser 40 is launched into a transmitting optical fiber 1, by means of a ×20 microscope objective 34. The fiber probe 9, is positioned above the surface of the excised eye lens 30, which is held in an ice bath 31, for the "cold" cataract experiment. The scattered light is collected by a receiving optical fiber 2, the free end of which is coupled to a photomultiplier 19. Photoelectron pulses from the photomultiplier 19 are processed and correlated using a computer based digital correlator 20. Results are displayed on a monitor 17. A stabilized high voltage supply 32 provides the biasing for the photomultiplier.

Figure 9:
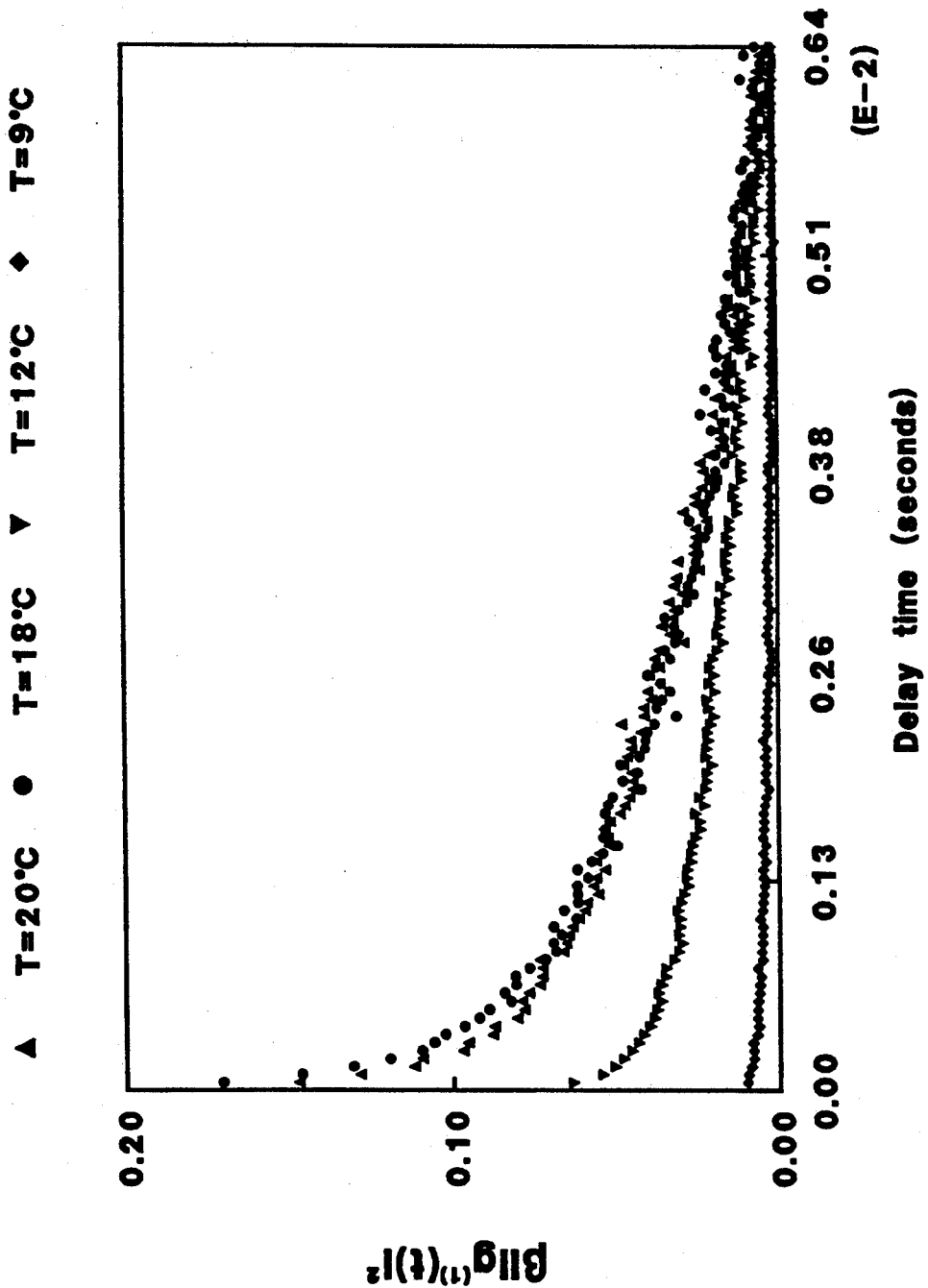
FIG. 9 is a graph illustrating a comparison of the normalized intensity-intensity autocorrelation, $\beta|g^{(1)}(t)|^2$, as the temperature is reduced in an excised bovine eye lens.
Figure 10:
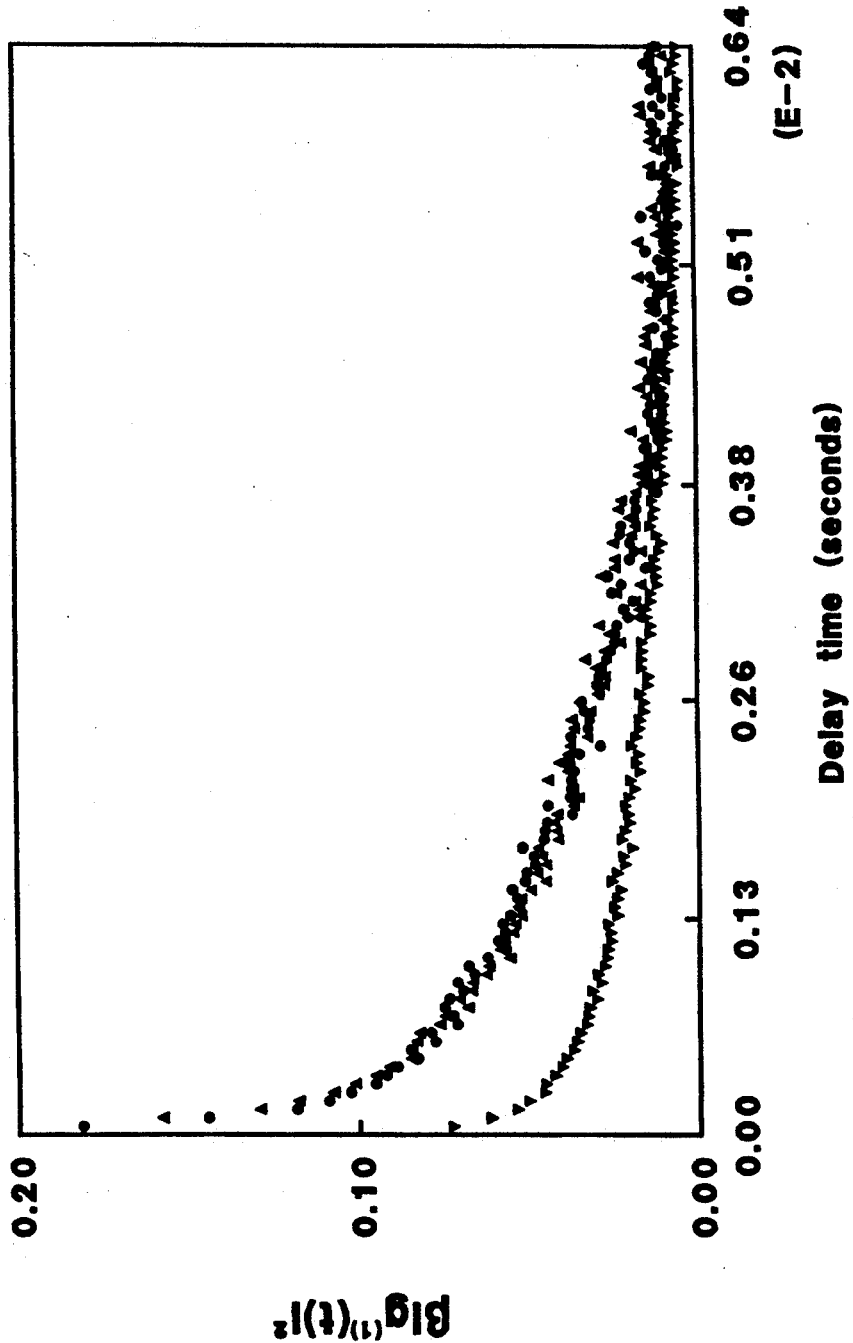
FIG. 10 is a graph illustrating a comparison of the normalized intensity-intensity autocorrelation, $\beta|g^{(1)}(t)|^2$, as the temperature is increased in an excised bovine eye lens.

FIG. 9 shows a comparison of the normalized autocorrelation functions obtained at various temperatures as the lens 30 was cooled by packed ice. A change in average size is clearly indicated by an increase in the correlation time, 1/e point of the curve. FIG. 10 shows the set of curves as the temperature was increased, showing that the lens recovers from the cataract to its initial transparency. For these measurements a probe with a scattering angle of 143° was used.

Figure 11:
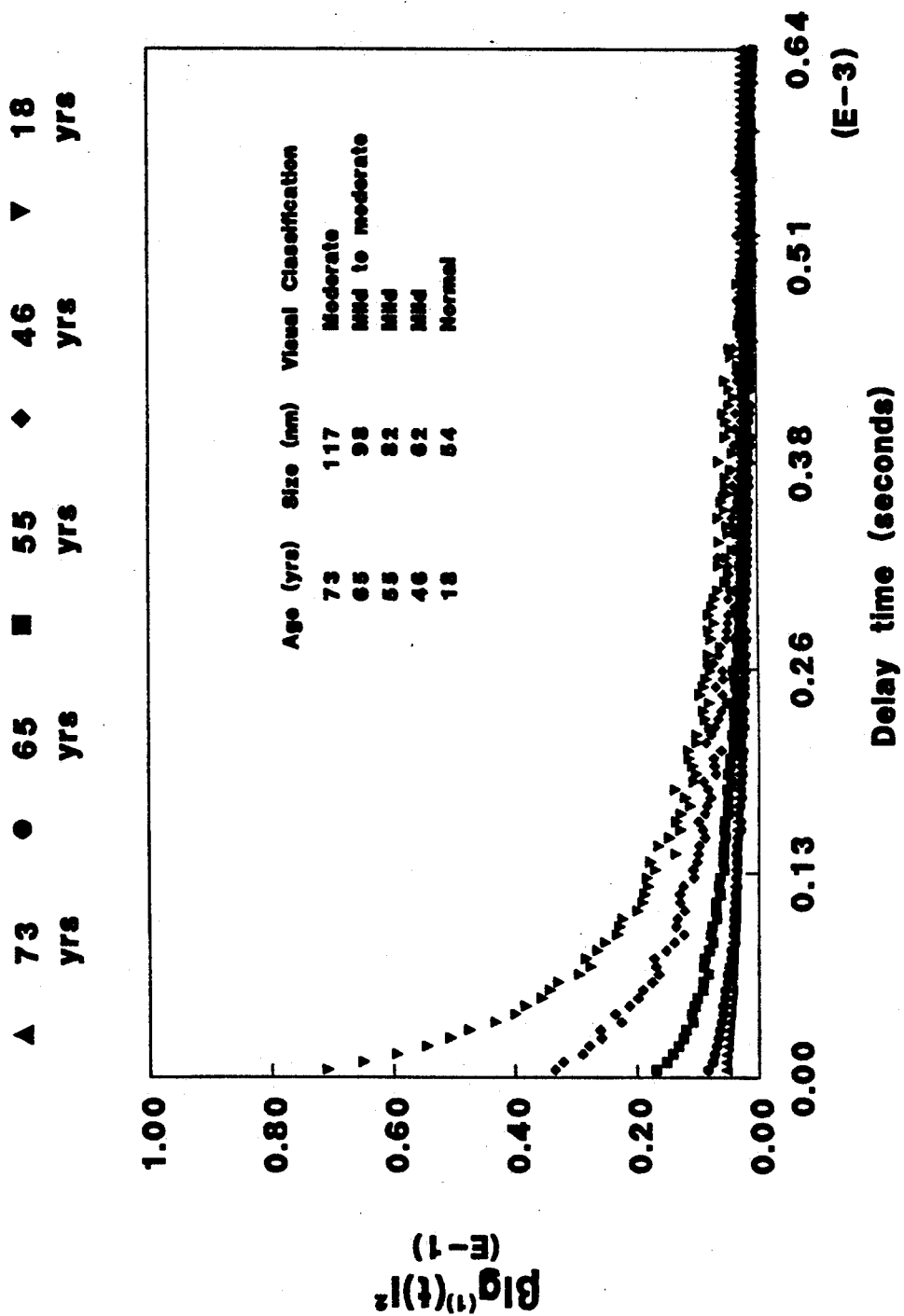
FIG. 11 is a graph illustrating a comparison of the normalized intensity-intensity autocorrelation, $\beta|g^{(1)}(t)|^2$, for various ages, in excised human eye lenses.
Figure 12:
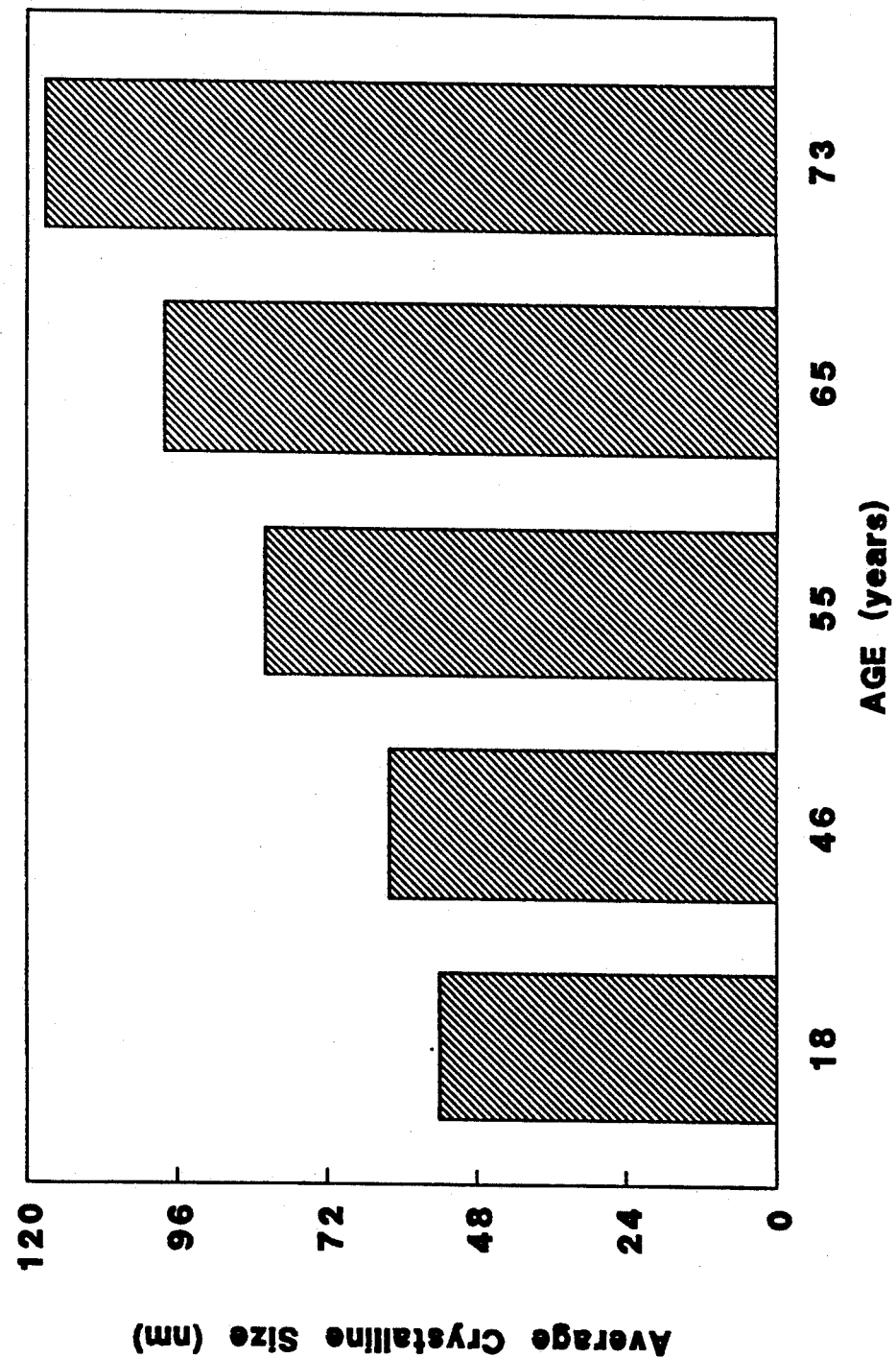
FIG. 12 is a histogram showing the average crystalline size as a function of age.

Five human eye lenses were excised from cadavers ranging in age from 18 to 73. Visual inspection indicated differences in transparency, or onset of cataractogenesis, in the older eyes. Another set of experiments, using a probe with a scattering angle of 155°, were performed using the apparatus shown in FIG. 8, and the results of autocorrelation measurements are plotted in FIG. 11 A standard cumulant analysis was used to determine the average diameter of the protein macromolecules in the eye lens. FIG. 12 shows a plot of the average diameter for various patients. These results correlate with visual observation. Repeated measurements on several days gave the same dependence. Other analysis techniques, such as non-negative least squares, or regularized inversion, usually give a distribution in size, and routinely can recover the presence of two distinct species. In this way, relative changes in the concentration and size of the various types of proteins can be tracked as a function of normal aging or drug therapy or diet therapy.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of determining the physical characteristics of ocular tissue comprising:
   providing a first optical fiber having a lens-less end;
   providing a second optical fiber having a lens-less end positioned in close proximity to the lens-less end of said first optical fiber;
   positioning the lens-less ends of said first and second optical fibers in close proximity to ocular tissue such that said lens-less ends are at a selected, non-parallel angle with respect to each other;

causing said first optical fiber to deliver an expanding beam of monochromatic laser light to said ocular tissue such that said light is back scattered by said ocular tissue into said lens-less end of said second optical fiber and said second optical fiber acts as a self-beating receiver of said scattered light;

converting said scattered light received by said second optical fiber into an electrical signal, and analyzing said electrical signals to determine whether changes in the molecular structure of the ocular tissue have occurred.

2. A method as described in claim 1 including the step of causing the propagation of a plurality of modes as the light scattered into said second optical fiber travels through said second optical fiber.

3. A method as described in claim 2 including the step of determining the first order electric field autocorrelation of the scattered light within said second optical fiber.

4. A method as described in claim 1 wherein said expanding beam is caused to be scattered by said ocular tissue at a scattering angle between about 90° and 175°.

5. A method as described in claim 1 including the step of replacing said first and second optical fibers with third and fourth optical fibers having lens-less ends positioned at a non-parallel angle with respect to each other which is different from said selected, non-parallel angle between the ends of said first and second optical fibers, whereby said monochromatic laser light is back scattered by a different portion of said ocular tissue than the ocular tissue which back scattered light from said first optical fiber.

6. A method as described in claim 1, wherein said first optical fiber is monomode at the wavelength of the monochromatic laser light.

7. A method as described in claim 6, wherein said second optical fiber is slightly multimode at the wavelength of the monochromatic laser light.

8. An assembly for determining the physical characteristics of ocular tissue, comprising:
a first optical fiber having a lens-less end;
a second optical fiber having a lens-less end for coherently detecting scattered light;
a probe housing, said housing including means for orienting said lens-less ends of said first and second optical fibers at a first selected, non-parallel angle with respect to each other and in close proximity to each other;
a laser connected to said first optical fiber, said laser including means for generating light of a selected wavelength, said first optical fiber being adapted for emitting an expanding monochromatic beam from said lens-less end thereof upon the generation of light of said selected wavelength by said laser;
a photodetector connected to said second optical fiber for converting back scattered light received by said lens-less end of said second optical fiber into electrical signals;
means connected to said photodetector for obtaining the first order electric field autocorrelation of the scattered light within said second optical fiber;
micropositioning means for positioning said probe such that the scattering volume of said probe can be precisely located, and
means for supporting said micropositioning means.

9. An assembly as described in claim 8 wherein said laser is a semiconductor laser, said first optical fiber being coupled to said laser.

10. An assembly as described in claim 8 wherein said second optical fiber is slightly multimode.

11. An assembly as described in claim 8 wherein said means for supporting said micropositioning means is an applanation tonometer mount.

12. An assembly as described in claim 6 wherein said probe housing includes first and second open ends, a face plate secured to said first open end of said housing, said face plate including first and second holes extending therethrough, said first and second holes extending at said first selected angle with respect to each other, said lens-less ends of said first and second optical fibers being positioned, respectively, within said first and second holes.

13. As assembly as described in claim 12, wherein said face plate includes an outer surface, said first and second optical fibers each having an end face coplanar with the outer surface of said face plate.

14. An assembly for determining the physical characteristics of ocular tissue, comprising:
a first optical fiber having a lens-less end;
a second optical fiber having a lens-less end for coherently detecting scattered light;
a probe housing, said housing including means for orienting said lens-less ends of said first and second optical fibers at a first selected, non-parallel angle with respect to each other and in close proximity to each other;
a semiconductor laser connected to said first optical fiber, said laser including means for generating light of a selected wavelength, said first optical fiber being adapted for emitting an expanding monochromatic beam from said lens-less end thereof upon the generation of light of said selected wavelength by said laser;
a photodetector connected to said second optical fiber for converting back scattered light received by said lens-less end of said second optical fiber into electrical signals;
means connected to said photodetector for obtaining the first order electric field autocorrelation of the scattered light within said second optical fiber;
micropositioning means for positioning said probe such that the scattering volume of said probe can be precisely located;
means for supporting said micropositioning means;
a microcomputer;
a first connector releasably coupling said semiconductor laser to said microcomputer, and
a second connector releasably coupling said second optical fiber to said photodetector.

15. An assembly as described in claim 14 including a third optical fiber having a lens-less end, a fourth optical fiber having a lens-less end, a second probe housing, said second probe housing, including means for orienting said lens-less ends of said third and fourth optical fibers at a second selected, non-parallel angle different from said first selected, non-parallel angle, a second semiconductor laser coupled to said third optical fiber, a third connector connected to said second semiconductor laser for releasably coupling said second semiconductor laser to said microcomputer, and a fourth connector connected to said fourth optical fiber for releasably coupling said fourth optical fiber to said photodetector.

* * * * *